(12) United States Patent
Funk et al.

(10) Patent No.: US 9,617,400 B2
(45) Date of Patent: *Apr. 11, 2017

(54) FRAGRANCED WATER-SENSITIVE FILM

(71) Applicant: Kimberly-Clark Worldwide, Inc., Neenah, WI (US)

(72) Inventors: Sarah A. Funk, Omro, WI (US); James Hongxue Wang, Shanghai (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/527,825

(22) Filed: Oct. 30, 2014

(65) Prior Publication Data

US 2015/0056461 A1 Feb. 26, 2015

Related U.S. Application Data

(62) Division of application No. 12/164,539, filed on Jun. 30, 2008.

(51) Int. Cl.
| | |
|---|---|
| *C08J 5/18* | (2006.01) |
| *A61F 13/84* | (2006.01) |
| *B29C 47/00* | (2006.01) |
| *B29C 47/10* | (2006.01) |
| *C08L 3/02* | (2006.01) |
| *B29C 47/88* | (2006.01) |
| *B29C 47/92* | (2006.01) |
| *C08K 5/05* | (2006.01) |
| *C08L 3/06* | (2006.01) |
| *C08L 3/08* | (2006.01) |
| *C08L 29/04* | (2006.01) |
| *C08L 67/00* | (2006.01) |
| *A61L 9/012* | (2006.01) |
| *B29K 105/00* | (2006.01) |

(52) U.S. Cl.
CPC ............ *C08J 5/18* (2013.01); *A61F 13/8405* (2013.01); *B29C 47/0021* (2013.01); *B29C 47/0026* (2013.01); *B29C 47/1081* (2013.01); *B29C 47/887* (2013.01); *B29C 47/8845* (2013.01); *B29C 47/8855* (2013.01); *B29C 47/8865* (2013.01); *B29C 47/8875* (2013.01); *B29C 47/92* (2013.01); *C08K 5/05* (2013.01); *C08L 3/02* (2013.01); *C08L 3/06* (2013.01); *C08L 3/08* (2013.01); *C08L 29/04* (2013.01); *C08L 67/00* (2013.01); *A61L 9/012* (2013.01); *B29C 47/1063* (2013.01); *B29C 2947/92704* (2013.01); *B29K 2105/0029* (2013.01); *C08J 2303/02* (2013.01); *C08J 2303/06* (2013.01); *C08J 2303/08* (2013.01); *C08J 2329/04* (2013.01); *C08K 2201/007* (2013.01); *C08L 2203/16* (2013.01); *Y10T 428/31855* (2015.04)

(58) Field of Classification Search
CPC ......................................................... C08J 5/18

USPC ............................................... 512/4; 523/102
See application file for complete search history.

(56) References Cited

U.S. PATENT DOCUMENTS

| | | |
|---|---|---|
| 3,137,592 A | 6/1964 | Protzman et al. |
| 3,655,129 A | 4/1972 | Seiner |
| 3,963,656 A | 6/1976 | Meisert et al. |
| 4,174,330 A | 11/1979 | Gilbert et al. |
| 4,209,417 A | 6/1980 | Whyte |
| 4,496,467 A | 1/1985 | Munteanu et al. |
| 4,761,437 A | 8/1988 | Christie |
| 4,797,468 A | 1/1989 | De Vries |
| 4,867,881 A | 9/1989 | Kinzer |
| 5,019,434 A | 5/1991 | Matsumoto |
| 5,028,648 A | 7/1991 | Famili et al. |
| 5,028,658 A | 7/1991 | David et al. |
| 5,093,422 A | 3/1992 | Himes |
| 5,102,465 A | 4/1992 | Lamond |
| 5,169,706 A | 12/1992 | Collier, IV et al. |

(Continued)

FOREIGN PATENT DOCUMENTS

| | | |
|---|---|---|
| EP | 0565386 A1 | 10/1993 |
| EP | 1384682 A3 | 1/2004 |
| EP | 1235879 B1 | 5/2004 |
| EP | 1075188 B1 | 11/2005 |
| WO | WO 0136535 A1 | 5/2001 |
| WO | WO 02053376 A2 | 7/2002 |
| WO | WO 02053376 A3 | 7/2002 |
| WO | WO 2004006967 A1 | 1/2004 |
| WO | WO 2005113616 A2 | 12/2005 |
| WO | WO 2005113616 A3 | 12/2005 |

OTHER PUBLICATIONS

ASTM D 1238-04c—*Standard Test Method for Melt Flow Rates of Thermoplastics by Extrusion Plastometer*, Current edition approved Dec. 1, 2004, Originally approved in 1965, pp. 1-14.

(Continued)

*Primary Examiner* — Peter F Godenschwager
(74) *Attorney, Agent, or Firm* — Dority & Manning, P.A.

(57) ABSTRACT

A film formed from a water-soluble polymer matrix containing a fragrance is provided. The film is water-sensitive so that upon contact with a sufficient amount of water, the matrix loses its integrity to increasingly expose the fragrance to the ambient environment for releasing its odor. The ability to incorporate a fragrance into the matrix is achieved by controlling the nature of the fragrance and polymer, the manner in which the matrix and fragrance are melt processed, etc. For example, the fragrance may be injected directly into the extruder and melt blended with the polymer to avoid the costly, time-consuming steps of pre-encapsulation or pre-compounding of the fragrance into a masterbatch. Furthermore, to balance the fragrance's ability to release the desired odor during use while minimizing the premature exhaustion of the odor during processing, the fragrance has a boiling point (at atmospheric pressure) of from about 125° C. to about 350° C.

15 Claims, 2 Drawing Sheets

(56) References Cited

U.S. PATENT DOCUMENTS

| | | |
|---|---|---|
| 5,292,783 A | 3/1994 | Buchanan et al. |
| 5,332,649 A | 7/1994 | Bleckmann et al. |
| 5,382,611 A | 1/1995 | Stepto et al. |
| 5,397,834 A | 3/1995 | Jane et al. |
| 5,446,079 A | 8/1995 | Buchanan et al. |
| 5,470,944 A | 11/1995 | Bonsignore |
| 5,523,293 A | 6/1996 | Jane et al. |
| 5,543,439 A | 8/1996 | McDermott et al. |
| 5,559,171 A | 9/1996 | Buchanan et al. |
| 5,580,911 A | 12/1996 | Buchanan et al. |
| 5,599,858 A | 2/1997 | Buchanan et al. |
| 5,605,961 A | 2/1997 | Lee et al. |
| 5,641,562 A | 6/1997 | Larson et al. |
| 5,665,152 A | 9/1997 | Bassi et al. |
| 5,747,648 A | 5/1998 | Bassi et al. |
| 5,770,682 A | 6/1998 | Ohara et al. |
| 5,817,721 A | 10/1998 | Warzelhan et al. |
| 5,821,327 A | 10/1998 | Oota et al. |
| 5,880,254 A | 3/1999 | Ohara et al. |
| 5,900,322 A | 5/1999 | Buchanan et al. |
| 5,910,545 A | 6/1999 | Tsai et al. |
| 5,922,379 A | 7/1999 | Wang |
| 5,939,192 A | 8/1999 | Rettenbacher et al. |
| 5,945,480 A | 8/1999 | Wang et al. |
| 5,965,708 A | 10/1999 | Bassi et al. |
| 5,977,312 A | 11/1999 | Bassi et al. |
| 5,981,012 A | 11/1999 | Pomplun et al. |
| 5,985,396 A | 11/1999 | Kerins et al. |
| 6,008,276 A | 12/1999 | Kalbe et al. |
| 6,020,425 A | 2/2000 | Wang et al. |
| 6,025,417 A | 2/2000 | Willett et al. |
| 6,063,866 A | 5/2000 | Wang et al. |
| 6,075,118 A | 6/2000 | Wang et al. |
| 6,096,809 A | 8/2000 | Lorcks et al. |
| 6,126,919 A | 10/2000 | Stefely et al. |
| 6,135,987 A | 10/2000 | Tsai et al. |
| 6,225,388 B1 | 5/2001 | Tsai et al. |
| 6,231,970 B1 | 5/2001 | Andersen et al. |
| 6,235,816 B1 | 5/2001 | Lorcks et al. |
| 6,258,924 B1 | 7/2001 | Warzelhan et al. |
| 6,296,914 B1 | 10/2001 | Kerins et al. |
| 6,297,347 B1 | 10/2001 | Warzelhan et al. |
| 6,326,458 B1 | 12/2001 | Gruber et al. |
| 6,350,518 B1 | 2/2002 | Schertz et al. |
| 6,369,215 B1 | 4/2002 | Peltonen et al. |
| 6,414,108 B1 | 7/2002 | Warzelhan et al. |
| 6,417,312 B1 | 7/2002 | Kirchmeyer et al. |
| 6,469,099 B1 | 10/2002 | Farah et al. |
| 6,517,625 B2 | 2/2003 | Bassi et al. |
| 6,530,910 B1 | 3/2003 | Pomplun et al. |
| 6,544,455 B1 | 4/2003 | Tsai et al. |
| 6,552,124 B2 | 4/2003 | Wang et al. |
| 6,552,162 B1 | 4/2003 | Wang et al. |
| 6,565,640 B1 | 5/2003 | Bengs et al. |
| 6,605,367 B2 | 8/2003 | Bassi et al. |
| 6,605,657 B1 | 8/2003 | Favis et al. |
| 6,660,211 B2 | 12/2003 | Topolkaraev et al. |
| 6,676,984 B1 | 1/2004 | Sharp et al. |
| 6,703,011 B2 | 3/2004 | Shefer et al. |
| 6,703,012 B1 | 3/2004 | White |
| 6,703,115 B2 | 3/2004 | Hale et al. |
| 6,709,671 B2 | 3/2004 | Zerbe et al. |
| 6,713,595 B2 | 3/2004 | Chung et al. |
| 6,727,342 B1 | 4/2004 | Bastioli et al. |
| 6,746,705 B2 | 6/2004 | Altieri et al. |
| 6,749,795 B2 | 6/2004 | Murphy |
| 6,767,961 B1 | 7/2004 | Wang et al. |
| 6,806,353 B2 | 10/2004 | Zhang et al. |
| 6,838,403 B2 | 1/2005 | Tsai et al. |
| 6,846,449 B2 | 1/2005 | Martin et al. |
| 6,890,989 B2 | 5/2005 | Wang et al. |
| 6,905,759 B2 | 6/2005 | Topolkaraev et al. |
| 6,921,581 B2 | 7/2005 | Van Gelder et al. |
| 6,933,335 B1 | 8/2005 | Berger et al. |
| 6,946,506 B2 | 9/2005 | Bond et al. |
| 6,958,371 B1 | 10/2005 | Wang et al. |
| 6,984,426 B2 | 1/2006 | Miksic et al. |
| 6,987,138 B2 | 1/2006 | Tokiwa et al. |
| 7,045,650 B2 | 5/2006 | Lawrey et al. |
| 7,053,151 B2 | 5/2006 | Wang et al. |
| 7,077,994 B2 | 7/2006 | Bond |
| 7,098,292 B2 | 8/2006 | Zhao et al. |
| 7,124,450 B2 | 10/2006 | Davidson |
| 7,153,354 B2 | 12/2006 | Narayan et al. |
| 7,153,569 B2 | 12/2006 | Kaufman et al. |
| 7,235,594 B2 | 6/2007 | Han et al. |
| 7,297,394 B2 | 11/2007 | Khemani et al. |
| 7,307,125 B2 | 12/2007 | Chundury et al. |
| 7,368,160 B2 | 5/2008 | Inglis |
| 7,402,618 B2 | 7/2008 | Xu |
| 7,413,731 B2 | 8/2008 | Heltovics et al. |
| 7,547,737 B2 | 6/2009 | Kochvar et al. |
| 7,998,888 B2 | 8/2011 | Shi et al. |
| 8,147,965 B2 | 4/2012 | Shi et al. |
| 8,188,185 B2 | 5/2012 | Wang et al. |
| 8,227,658 B2 | 7/2012 | Shi et al. |
| 8,283,006 B2 | 10/2012 | Wang et al. |
| 8,329,601 B2 | 12/2012 | Shi et al. |
| 8,329,977 B2 * | 12/2012 | Wang .................. C08J 5/18 523/111 |
| 8,334,327 B2 | 12/2012 | Kaufman et al. |
| 8,338,508 B2 | 12/2012 | Shi et al. |
| 8,445,110 B2 | 5/2013 | Shi et al. |
| 8,759,279 B2 | 6/2014 | Funk et al. |
| 2002/0098341 A1 | 7/2002 | Schiffer et al. |
| 2003/0077395 A1 | 4/2003 | Bassi et al. |
| 2003/0099692 A1 | 5/2003 | Lydzinski et al. |
| 2003/0232933 A1 | 12/2003 | Lagneaux et al. |
| 2004/0034149 A1 | 2/2004 | Garcia |
| 2004/0108611 A1 | 6/2004 | Dennis et al. |
| 2004/0253434 A1 | 12/2004 | Patel et al. |
| 2005/0079372 A1 | 4/2005 | Schmal et al. |
| 2005/0186256 A1 | 8/2005 | Dihel et al. |
| 2005/0208294 A1 | 9/2005 | Kaufman et al. |
| 2005/0244606 A1 | 11/2005 | Egawa |
| 2006/0135728 A1 | 6/2006 | Peerlings et al. |
| 2006/0149199 A1 | 7/2006 | Topolkaraev et al. |
| 2007/0031555 A1 | 2/2007 | Axelrod et al. |
| 2007/0049685 A1 | 3/2007 | Hansel et al. |
| 2007/0049719 A1 | 3/2007 | Brauer et al. |
| 2007/0129467 A1 | 6/2007 | Scheer |
| 2007/0213412 A1 * | 9/2007 | Bacon et al. .................. 516/53 |
| 2007/0246867 A1 | 10/2007 | Nelson et al. |
| 2007/0298237 A1 | 12/2007 | Goino et al. |
| 2008/0147034 A1 | 6/2008 | Wang et al. |
| 2009/0054548 A1 | 2/2009 | Wang et al. |
| 2012/0225966 A1 | 9/2012 | Shi et al. |

OTHER PUBLICATIONS

ASTM D 1343-56—*Standard Method of Test for Viscosity of Cellulose Derivatives by Ball-Drop Method*, Adopted 1956, pp. 486-489.

ASTM D 1505-03—*Standard Test Method for Density of Plastics by the Density-Gradient Technique*, Current edition approved Nov. 1, 2003, Originally approved in 1957, pp. 1-7.

ASTM D 1525-07—*Standard Test Method for Vicat Softening Temperature of Plastics*, Current edition approved Mar. 1, 2007, Originally approved in 1958, pp. 1-9.

ASTM D 3418-03 (D 3417-99)—*Standard Test Method for Transition Temperatures and Enthalpies of Fusion and Crystallization of Polymers by Differential Scanning Calorimetry*, Current edition approved Dec. 1, 2003, Originally approved in 1976, pp. 66-72.

ASTM D 3806-98 (Reapproved 2004)—*Standard Test Method of Small-Scale Evaluation of Fire-Retardant Paints (2-Foot Tunnel Method)*, Current edition approved Jun. 1, 2004, Originally approved in 1979, pp. 1-6.

ASTM D 5034-95—*Standard Test Method for Breaking Strength and Elongation of Textile Fabrics (Grab Test)*, Current edition approved May 15, 1995, pp. 674-681.

ASTM D 5338-92—*Standard Test Method for Determining Aerobic Biodegradation of Plastic Materials Under Controlled Composting Conditions*, Current edition approved Dec. 15, 1992, pp. 456-461.

(56) References Cited

OTHER PUBLICATIONS

ASTM D 638 08—*Standard Test Method for Tensile Properties of Plastics*, Current edition approved Apr. 1, 2008, Originally approved in 1941, pp. 1-16.
ASTM D 790-99—*Standard Test Methods for Flexural Properties of Unreinforced and Reinforced Plastics and Electrical Insulating Materials*, Current edition approved Nov. 10, 1999, pp. 150-158.
Abstract of Japanese Patent No. JP2007137847 dated Jun. 1, 2006, 1 page.
Abstract of Japanese Patent No. JP2006505719 dated Feb. 16, 2006, 1 page.
Article—*Aging Properties of Films of Plasticized Vital Wheat Gluten Cast from Acidic and Basic Solutions*, Olabarrieta et al., Biomacromolecules, vol. 7, No. 5, 2006, pp. 1657-1664.
Article—*Biodegradable Compositions by Reactive Processing of Aliphatic Polyester/Polysaccharide Blends*, Dubois et al., Macromol. Symp., vol. 198, 2003, pp. 233-243.
Article—*Biodegradable Soy Protein-Polyester Blends by Reactive Extrusion Process*, Graiver et al., Journal of Applied Polymer Science, vol. 92, 2004, pp. 3231-3239.
Article—*Chemical Modification of Starch*, Tomasik et al., Advances in Carbohydrate Chemistry and Biochemistry, vol. 59, 2004, pp. 175-316.
Article—*Edible Protein Films and Coatings*, Food Proteins and Their Applications edited by S. Damodaran and A. Paraf, John M. Krochta, 1997, pp. 529-539.
Article—*Effects of Extruder Die Nozzle Dimensions on Expansion and Micrographic Characterization During Extrusion of Acetylated Starch*, Ganjyal et al., Starch/Stärke, vol. 56, 2004, pp. 108-117.
Article—*Extrusion of Wheat Gluten Plasticized with Glycerol: Influence of Process Conditions on Flow Behavior, Rheological Properties and Molecular Size Distribution*, Redl et al., Cereal Chemistry, vol. 76, No. 3, 1999, pp. 361-370.
Article—*Glycol Glucosides from Starch by Continuous Twin-Screw Extruder Processing*, Carr et al., Cereal Chemistry, vol. 66, No. 3, 1989, pp. 238-243.
Article—*Heat and shear mediated polymerization of plasticized wheat gluten protein upon mixing*, Redl et al., Journal of Cereal Science 38, 2003, pp. 105-114.
Article—*Polyurethane/Polyolefin Blends: Morphology, Compatibilization and Mechanical Properties*, Wang et al., Polymers & Polymer Composites, vol. 14, No. 1, 2006, 11 pages.
Article—*Preparation of Acetylated Distarch Adipates by Extrusion*, Mail et al., Lebensmittel-Wissenschaft und-Technologie, vol. 34, No. 6, 2001, pp. 384-389.
Article—*Reactivity of Wheat Gluten Protein during Mechanical Mixing: Radical and Nucleophilic Reactions for the Addition of Molecules on Sulfur*, Auvergne et al., Biomacromolecules, vol. 9, No. 2, 2008, pp. 664-671.
Article—*Soy Protein-Based Biodegradable Plastics*, Mungara et al., Proceedings in Plastics Impact on the Environment Conference, Society of Plastic, Feb. 2003, pp. 393-397.
Article—*Starch Modification, Destruction and Hydrolysis during O-Formylation*, Divers et al., Starch/Stärke 56, 2004, pp. 389-398.
Article—*The chemical modification of a range of starches under aqueous reaction conditions*, Fang et al., Carbohydrate Polymers 55, 2004, pp. 283-289.
Article—*The History of Tomorrow's Materials: Protein-Based Biopolymers*, Ralston et al., Plastics Engineering, Feb. 2008, pp. 36-40.
Article—*The Hydroxypropylation of Starch in a Self-Wiping Twin Screw Extruder*, De Graaf et al., Advances in Polymer Technology, vol. 22, No. 1, 2003, pp. 56-68.
Article—*Thermoplastic Processing of Protein-Based Bioplastics: Chemical Engineering Aspects of Mixing, Extrusion and Hot Molding*, Pommet et al., Macromol. Symp. vol. 197, 2003, pp. 207-217.
Article—*Thermoplastic Processing of Proteins for Film Formation—A Review*, Hernandez-Izquierdo et al., Journal of Food Science, vol. 73, No. 2, 2008, pp. R30-R39.
Methyl Salicylate 119-36-9 Product Reference, The Good Scents Company, May 2009, 13 pages, www.thegoodscentscompany.com/data/rw1008471.html.
Ethyl Salicylate 118-61-6 Product Reference, The Good Scents Company, May 2009, 6 pages, www.thegoodscentscompany.com/data/rw1001561.html.
Cedarwood Oil Virginia Product Reference, The Good Scents Company, May 2009, 8 pages, www.thegoodscentscompany.com/data/es1002991.html.
Search Report and Written Opinion for PCT/IB2009/052015 dated Jan. 22, 2010, 13 pages.

\* cited by examiner

FRAGRANCED WATER-SENSITIVE FILM

RELATED APPLICATIONS

The present application is a divisional of U.S. application Ser. No. 12/164,539 having a filing date of Jun. 30, 2008, the entire contents of which is incorporated herein by reference.

BACKGROUND OF THE INVENTION

Films are employed in a wide variety of disposable goods, such as diapers, sanitary napkins, adult incontinence garments, bandages, packaging, etc. In this regards, various attempts have been made to incorporate fragrances into films so that they are capable of releasing a desirable odor. For example, fragrances have been added to packaging films and bags to counteract malodor associated with certain applications (e.g., garbage disposal), U.S. Patent Application No. 2003/0204001 to Van Gelder, et al., for example, describes a method for producing a polyethylene or polypropylene film having a fragrance. The film is formed by adding a liquid fragrance to porous pellets of polyethylene or polypropylene, blending the mixture with an odor barrier (e.g., bis-fatty acid amide), and then extruding the blend into pellets to form a "masterbatch." The masterbatch may subsequently be mixed with a polyethylene or polypropylene polymer at a ratio of 100:1 to 20:1 (ratio of polymer to masterbatch) to form a film. Unfortunately, however, such techniques are overly complex and costly in that they first require the formation of a masterbatch and they also require the use of an odor barrier to prevent premature evaporation of the fragrance.

Attempts have also been made to incorporate additives into films so that the additive is released only upon disintegration of the film. For example, U.S. Patent Application Publication No. 2005/0186256 to Dihel, et al, describes a film used to deliver a substance (e.g., flavor) that is encapsulated in a water-soluble encapsulant. The encapsulated substance is sprinkled or dusted onto the dissolvable film. Such techniques are, however, problematic in much the same manner as referenced above. For example, the technique first requires that the substance is pre-encapsulated, which adds an unnecessary level of complexity and cost to the manufacturing process.

As such, a need currently exists for an improved technique for incorporating a fragrance into a film.

SUMMARY OF THE INVENTION

In accordance with one embodiment of the present invention, a method for forming a fragranced film is disclosed that comprises supplying at least one water-soluble polymer to an extruder; injecting at least one liquid fragrance into the extruder to form a blend comprising the water-soluble polymer and the fragrance, wherein the liquid fragrance has a boiling point at atmospheric pressure of from about 125° C. to about 350° C.; and extruding the blend onto a surface to form a film.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
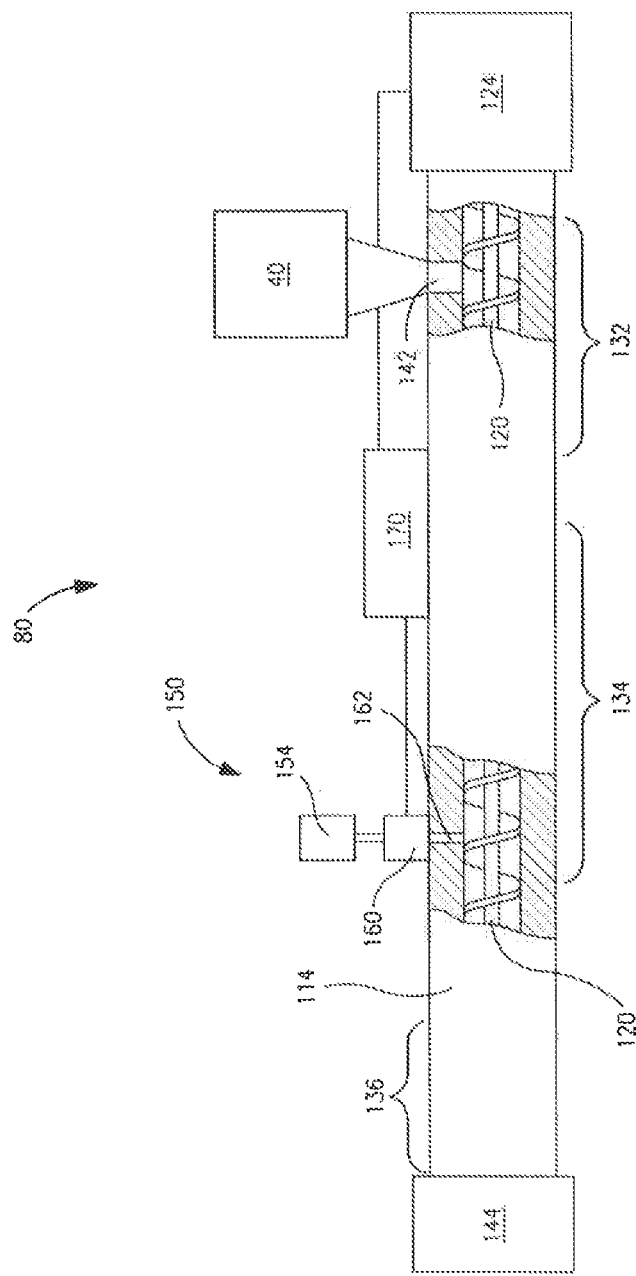
FIG. 1 is a partially broken away side view of an extruder that may be used in one embodiment of the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a film formed from a water-soluble polymer matrix within which is contained at least one fragrance. The film is water-sensitive (e.g., water-soluble, water-dispersible, etc.) so that upon contact with a sufficient amount of water, the polymer matrix loses its integrity over time to increasingly expose the fragrance to the ambient environment for releasing its odor. The ability to incorporate a fragrance into the polymer matrix is achieved in the present invention by controlling a variety of aspects of the film construction, including the nature of the fragrance, the nature of the water-soluble polymer, the manner in which the polymer matrix and fragrance are melt processed, etc. For example, the fragrance may be injected directly into the extruder and melt blended with the water-soluble polymer. In this manner, the costly and time-consuming steps of pre-encapsulation or pre-compounding of the fragrance into a masterbatch are not required. Furthermore, to obtain a balance between the ability of the fragrance to release the desired odor during use and likewise to minimize the premature exhaustion of the odor during melt processing, the fragrance is selected to have a boiling point (at atmospheric pressure) within a certain range, such as from about 125° C. to about 350° C.

In this regard, various embodiments of the present invention will now be described in more detail below.

I. Film Components

A. Fragrance

Although any number of fragrances may generally be employed in the film of the present invention to produce the desired odor, at least one fragrance is employed that is in the form of a liquid at ambient temperature and pressure. The boiling point of such a liquid fragrance is normally selected within a certain range so that it is volatile enough to produce the desired odor, but not to such an extent that a significant portion of the fragrance is released during melt processing of the film. In this regard, the fragrance typically has a boiling point (at atmospheric pressure) of from about 125° C. to about 350° C., in some embodiments, from about 150° C. to about 300° C., and in some embodiments, from about 175° C. to about 250° C. Some examples of such fragrances may include, for instance, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate, etc., and mixtures thereof.

Of course, other fragrances may also be employed in the present invention as is well known in the art. For example, such fragrances may include anethol, methyl heptine carbonate, ethyl aceto acetate, pare cymene, neral, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde, phenyl acetaldehyde, anisic aldehyde, benzyl acetone, ethyl-2-methyl butyrate, damascenone, damascone alpha, damascone beta, floc acetate, frutene, fructone, herbavert, isocyclo citral, methyl isobutenyl tetrahydro pyran, isopropyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, cis 1,3-oxathiane-2-methyl-4-propyl, etc., and mixtures thereof. Still other suitable fragrances are described in U.S. Pat. Nos. 4,145,184; 4,209,417; 4,515,705; and 4,152,272, all of which are incorporated herein in their entirety by reference thereto for all purposes.

B. Water-Soluble Polymer

The film of the present invention also contains one or more water-soluble polymers that form a polymer matrix within which the fragrance is contained prior to disintegration of the film. In one particular embodiment, the water-soluble polymer contains a repeating unit having a functional hydroxyl group, such as vinyl alcohol homopolymers (e.g., "PVOH"), vinyl alcohol copolymers (e.g., ethylene vinyl alcohol copolymers, methyl methacrylate vinyl alcohol copolymers, etc.), etc. Vinyl alcohol polymers, for instance, have at least two or more vinyl alcohol units in the molecule and may be a homopolymer of vinyl alcohol, or a copolymer containing other monomer units. Vinyl alcohol homopolymers may be obtained by hydrolysis of a vinyl ester polymer, such as vinyl formate, vinyl acetate, vinyl propionate, etc. Vinyl alcohol copolymers may be obtained by hydrolysis of a copolymer of a vinyl ester with an olefin having 2 to 30 carbon atoms, such as ethylene, propylene, 1-butene, etc.; an unsaturated carboxylic acid having 3 to 30 carbon atoms, such as acrylic acid, methacrylic acid, crotonic acid, maleic acid, fumaric acid, etc., or an ester, salt, anhydride or amide thereof; an unsaturated nitrile having 3 to 30 carbon atoms, such as acrylonitrile, methacrylonitrile, etc.; a vinyl ether having 3 to 30 carbon atoms, such as methyl vinyl ether, ethyl vinyl ether, etc.; and so forth.

The degree of hydrolysis may be selected to optimize solubility, etc., of the polymer. For example, the degree of hydrolysis may be from about 60 mole % to about 95 mole %, in some embodiments from about 80 mole % to about 90 mole %, and in some embodiments, from about 85 mole % to about 89 mole %. Examples of suitable partially hydrolyzed polyvinyl alcohol polymers are available under the designation CELVOL™ 203, 205, 502, 504, 508, 513, 518, 523, 530, or 540 from Celanese Corp. Other suitable partially hydrolyzed polyvinyl alcohol polymers are available under the designation ELVANOL™ 50-14, 50-26, 50-42, 51-03, 51-04, 51-05, 51-08, and 52-22 from DuPont.

In addition to the polymers discussed above, other water-soluble polymers may also be employed in the present invention. For example, water-soluble polymers may also be formed from monomers such as vinyl pyrrolidone, hydroxyethyl acrylate or methacrylate (e.g., 2-hydroxyethyl methacrylate), hydroxypropyl acrylate or methacrylate, acrylic or methacrylic acid, acrylic or methacrylic esters or vinyl pyridine, acrylamide, vinyl acetate, ethylene oxide, derivatives thereof, and so forth. Mixes or blends of two or more water soluble polymers may also be used in this invention to provide balanced water-solubility, melt processability, mechanical properties and or physical properties. Example of the blends of water soluble polymers include blends of polyvinyl alcohol and polyethylene oxide as disclosed in U.S. Pat. No. 6,958,371 to Wang, et al. Other examples of suitable monomers are described in U.S. Pat. No. 4,499,154 to James, et al., which is incorporated herein in its entirety by reference thereto for all purposes.

Starches may also be employed that have been chemically modified (e.g., esterification, etherification, oxidation, enzymatic hydrolysis, etc.) to render them generally soluble in water. Starch ethers and/or esters may be particularly desirable, such as hydroxyalkyl starches, carboxymethyl starches, etc. The hydroxyalkyl group of hydroxylalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch. The source of the starch may vary, but typically includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm.

The water-soluble polymers generally have a relatively low viscosity to enhance their melt compatibility with the fragrances. In this manner, the resulting film may be formed that is substantially free of distinct phases that might otherwise cause the fragrance to act as a barrier and limit the ability of the water-soluble polymer to contact water and thereby disperse. For example, the water-soluble polymers may have a solution viscosity of from about 50 to about 800 milliPascal seconds (mPa·s), in some embodiments from about 100 to about 700 mPa·s, and in some embodiments, from about 200 to about 600 mPa·s. The solution viscosity is measured as a 4 percent aqueous solution at 20° C. by the Hoeppler falling ball method in accordance with ASTM-D 1343-56 Part 8, 1958, page 486.

The molecular weight of the polymers may be selected to achieve the desired viscosity. Vinyl alcohol polymers, for instance, typically have a number average molecular weight ("$M_n$") ranging from about 1,000 to about 80,000 grams per mole, in some embodiments from about 5,000 to about 60,000 grams per mole, and in some embodiments, from about 10,000 to about 40,000 grams per mole. Likewise, vinyl alcohol polymers may also have a weight average molecular weight ("$M_w$") ranging from about 10,000 to about 150,000 grams per mole, in some embodiments from about 20,000 to about 100,000 grams per mole, and in some embodiments, from about 30,000 to about 75,000 grams per mole. Starches, on the other hand, may have a higher molecular weight, such as a number average molecular weight ("$M_n$") of from about 50,000 to about 1,000,000 grams per mole, in some embodiments from about 75,000 to about 800,000 grams per mole, and in some embodiments, from about 100,000 to about 600,000 grams per mole, as well as a weight average molecular weight ("$M_w$") ranging from about 5,000,000 to about 25,000,000 grams per mole, in some embodiments from about 5,500,000 to about 15,000,000 grams per mole, and in some embodiments, from about 6,000,000 to about 12,000,000 grams per mole.

Regardless of the particular polymers employed, a plasticizer may also be employed in the present invention to help render the water-soluble polymer melt-processible. Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

Typically, the weight ratio of water-soluble polymers to plasticizers in the film may be from about 1 to about 50, in some embodiments from about 2 to about 25, and in some embodiments, from about 3 to about 15. For example, a blend of plasticizer and water-soluble polymer ("plasticized water-soluble polymer") may contain from about 1 wt. % to about 40 wt. %, in some embodiments from about 2 wt. % to about 30 wt. %, and in some embodiments, from about 5 wt. % to about 25 wt. % of plasticizers, and also from about 60 wt. % to about 99 wt. %, in some embodiments from about 70 wt. % to about 98 wt. %, and in some embodiments, from about 75 wt. % to about 95 wt % of water-soluble polymers.

Through selective control over the nature of the water-soluble polymer (e.g., molecular weight, viscosity, etc.), the nature of the plasticizer, and the relative amounts of the water-soluble polymer and plasticizer, the resulting plasticized water-soluble polymer may achieve a melt viscosity that is compatible with the fragrance, which further helps minimize phase separation during formation of the film. For example, the plasticized water-soluble polymer may have an apparent melt viscosity of from about 10 to about 400 Pascal seconds (Pa·s), in some embodiments from about 20 to about 200 Pa·s, and in some embodiments, from about 30 to about 100 Pa·s, as determined at a temperature of 195° C. and a shear rate of 1000 sec$^{-1}$.

The relative amount of the water-soluble polymers and fragrances employed in the film may also be selected to help further minimize phase separation. For example, the weight ratio of water-soluble polymers to fragrances is typically from about 1 to about 500, in some embodiments from about 10 to about 200, and in some embodiments, from about 20 to about 80. Fragrances, for example, may constitute from about 0.1 wt. % to about 15 wt. %, in some embodiments from about 0.5 wt. % to about 10 wt. %, and in some embodiments, from about 1 wt. % to about 5 wt. % of the film. Water-soluble polymers may constitute from about 40 wt. % to about 99.9 wt. %, in some embodiments from about 50 wt % to about 99.5 wt. %, and in some embodiments, from about 60 wt. % to about 99 wt. % of the film. Likewise, when employed, plasticizers may constitute from about 1 wt. % to about 30 wt. %, in some embodiments from about 2 wt. % to about 25 wt %, and in some embodiments, from about 5 wt. % to about 20 wt. % of the film.

C. Other Components

Other components may also be incorporated into the film as is known in the art. For example, the film may contain one or more biodegradable polyesters, The term "biodegradable" generally refers to a material that degrades from the action of naturally occurring microorganisms, such as bacteria, fungi, and algae; environmental heat; moisture; or other environmental factors, such as determined according to ASTM Test Method 5338.92. Examples of suitable biodegradable polyesters include aliphatic polyesters, such as polycaprolactone, polyesteramides, modified polyethylene terephthalate, polylactic acid (PLA) and its copolymers, terpolymers based on polylactic acid, polyglycolic acid, polyalkylene carbonates (such as polyethylene carbonate), polyhydroxyalkanoates (PHA), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aromatic polyesters and modified aromatic polyesters; and aliphatic-aromatic copolyesters. For example, the biodegradable polyester may be an aliphatic-aromatic copolyester having the following structure:

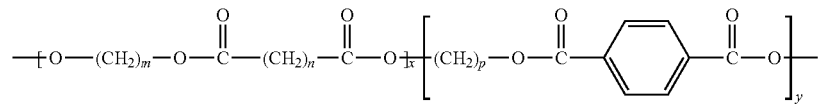

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1; and y is an integer greater than 1. One example of such a copolyester is polybutylene adipate terephthalate, which is commercially available under the designation ECOFLEX® F BX 7011 from BASF Corp. Another example of a suitable copolyester containing an aromatic terephtalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes. When employed, biodegradable polyesters typically constitute from about 1 wt % to about 40 wt. %, in some embodiments from about 2 wt. % to about 35 wt %, and in some embodiments, from about 5 wt. % to about 30 wt. % of the film.

In addition to the components noted above, other additives may also be incorporated into the film of the present invention, such as slip additives (e.g., fatty acid salts, fatty acid amides, etc.), compatibilizers (e.g., functionalized polyolefins), dispersion aids, melt stabilizers, processing stabilizers, heat stabilizers, light stabilizers, antioxidants, heat aging stabilizers, whitening agents, antiblocking agents, bonding agents, lubricants, fillers, etc. Dispersion aids, for instance, may also be employed to help create a uniform dispersion of the water-soluble polymer/fragrance mixture and retard or prevent separation into constituent phases. Likewise, the dispersion aids may also improve the water dispersibility of the film. When employed, the dispersion aid(s) typically constitute from about 0.01 wt. % to about 15 wt. %, in some embodiments from about 0.1 wt. % to about 10 wt. %, and in some embodiments, from about 0.5 wt. % to about 5 wt. % of the film. Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

Fillers may also be employed in the present invention. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.: U.S. Pat. No. 6,461,457 to Taylor, et al., which are incorporated herein in their entirety by reference thereto for all purposes. Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven webs). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack, which are incorporated herein in their entirety by reference thereto for all purposes.

II. Film Construction

As indicated above, the fragrance is typically injected in a liquid form directly into the extruder and melt blended with the water-soluble polymer. In this manner, the costly and time-consuming steps of pre-encapsulation or pre-compounding of the fragrance are not required. Referring to FIG. 1, for example, one embodiment of an extruder 80 that may be employed for this purpose is illustrated. As shown, the extruder 80 contains a housing or barrel 114 and a screw 120 (e.g., barrier screw) rotatably driven on one end by a suitable drive 124 (typically including a motor and gearbox). If desired, a twin-screw extruder may be employed that contains two separate screws. The extruder 80 generally contains three sections: the feed section 132, the melt section 134, and the mixing section 136. The feed section 132 is the input portion of the barrel 114 where the plastic material is added. The melt section 134 is the phase change section in which the plastic material is changed from a solid to a liquid. The mixing section 136 is adjacent the output end of the barrel 114 and is the portion in which the liquid plastic material is completely mixed. While there is no precisely defined delineation of these sections when the extruder is manufactured, it is well within the ordinary skill of those in this art to reliably identify the melt section 134 of the extruder barrel 114 in which phase change from solid to liquid is occurring.

A hopper 40 is also located adjacent to the drive 124 for supplying the water-soluble polymer and/or other materials (e.g., plasticizer) through an opening 142 in the barrel 114 to the feed section 132. Opposite the drive 124 is the output end 144 of the extruder 80, where extruded plastic is output for further processing to form a film, which will be described in more detail below. A liquid fragrance supply station 150 is also provided on the extruder barrel 114 that includes at least one hopper 154, which is attached to a pump 160 to selectively provide the liquid fragrance through an opening 162 to the melt section 134. In this manner, the fragrance may be mixed with the water-soluble polymer in a consistent and uniform manner. Of course, in addition to or in lieu of supplying the liquid fragrance to the melt section 134, it should also be understood that the liquid fragrance may be supplied to other sections of the extruder, such as the feed section 132 and/or the mixing section 136.

The pump 160 may be a high pressure pump (e.g., positive displacement pump) with an injection valve so as to provide a steady selected amount of fragrance to the barrel 114. If desired, a programmable logic controller 170 may also be employed to connect the drive 124 to the pump 160 so that it provides a selected volume of fragrance based on the drive rate of the screw 120. That is, the controller 170 may control the rate of rotation of the drive screw 120 and the pump 160 to inject the fragrance at a rate based on the screw rotation rate. Accordingly, if the rotation rate of the screw 120 is increased to drive greater amounts of plastic through the barrel 114 in a given unit of time, the pumping rate of the pump 160 may be similarly increased to pump proportionately greater amounts of fragrance into the barrel 114.

Once injected into the extruder 80, the fragrance and water-soluble polymer may be blended under high shear/pressure and heat to ensure sufficient mixing. For example, melt blending may occur at a temperature of from about 75° C. to about 350° C., in some embodiments, from about 100° C. to about 300° C., and in some embodiments, from about 150° C. to about 250° C. Likewise, the apparent shear rate during melt blending may range from about 100 seconds$^{-1}$ to about 10,000 seconds$^{-1}$ in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

Any known technique may be used to form a film from the blended material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. In yet another embodiment, however, the film is formed using a casting technique.

Figure 2:
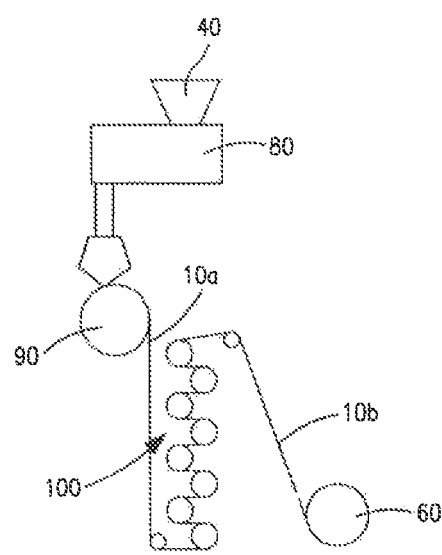
FIG. 2 is a schematic illustration of one embodiment of a method for forming a film in accordance with the present invention.

Referring to FIG. 2, for instance, one embodiment of a method for forming a cast film is shown. In this embodiment, the raw materials (not shown) are supplied to the extruder 80 in the manner described above and shown in FIG. 1, and then cast onto a casting roll 90 to form a single-layered precursor film 10*a*. If a multilayered film is to be produced, the multiple layers are co-extruded together onto the casting roll 90. The casting roll 90 may optionally be provided with embossing elements to impart a pattern to the film. Typically, the casting roll 90 is kept at temperature sufficient to solidify and quench the sheet 10*a* as it is formed, such as from about 20 to 60° C. If desired, a vacuum box may be positioned adjacent to the casting roll 90 to help keep the precursor film 10*a* close to the surface of the roll 90. Additionally, air knives or electrostatic pinners may help force the precursor film 10*a* against the surface of the casting roll 90 as it moves around a spinning roll. An air knife is a device known in the art that focuses a stream of air at a very high flow rate to pin the edges of the film.

Once cast, the film 10*a* may then be optionally oriented in one or more directions to further improve film uniformity and reduce thickness. Orientation may also form micropores in a film containing a filler, thus providing breathability to the film. For example, the film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" oriented film may then be laminated to a fibrous web. In addition, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 2, for instance, one method for forming a uniaxially oriented film is shown. As illustrated, the precursor film 10*a* is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 2. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10*a* above room temperature (e.g., to 125° F.). The progressively faster speeds of adjacent rolls in the MDO act to stretch the film 10*a*. The rate at which the stretch rolls rotate determines the amount of stretch in the film and final film weight.

The resulting film 10*b* may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

The thickness of the resulting water-sensitive film may generally vary depending upon the desired use. Nevertheless, the film thickness is typically minimized to reduce the time needed for the film to disperse in water. Thus, in most embodiments of the present invention, the water-sensitive film has a thickness of about 50 micrometers or less, in some embodiments from about 1 to about 100 micrometers, in some embodiments from about 5 to about 75 micrometers, and in some embodiments, from about 10 to about 60 micrometers.

Despite having such a small thickness and good sensitivity in water, the film of the present invention is nevertheless able to retain good dry mechanical properties during use. One parameter that is indicative of the relative dry strength of the film is the ultimate tensile strength, which is equal to the peak stress obtained in a stress-strain curve. Desirably, the film of the present invention exhibits an ultimate tensile strength in the machine direction ("MD") of from about 1 to about 50 Megapascals (MPa), in some embodiments from about 5 to about 40 MPa, and in some embodiments, from about 10 to about 30 MPa, and an ultimate tensile strength in the cross-machine direction ("CD") of from about 1 to about 50 Megapascals (MPa), in some embodiments from about 5 to about 40 MPa, and in some embodiments, from about 10 to about 30 MPa. Although possessing good strength, it is also desirable that the film is not too stiff. One parameter that is indicative of the relative stiffness of the film (when dry) is Young's modulus of elasticity, which is equal to the ratio of the tensile stress to the tensile strain and is determined from the slope of a stress-strain curve. For example, the film typically exhibits a Young's modulus in the machine direction ("MD") of from about 100 to about 1500 Megapascals ("MPa"), in some embodiments from about 200 to about 1000 MPa, and in some embodiments, from about 300 to about 900 MPa, and a Young's modulus in the cross-machine direction ("CD") of from about 75 to about 1200 Megapascals ("MPa"), in some embodiments from about 175 to about 900 MPa, and in some embodiments, from about 250 to about 850 MPa.

The film of the present invention may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a blend of the water-soluble polymer and fragrance. In most embodiments, the skin layer(s) are also formed from the blend as described above. It should be understood, however, that other polymers may also be employed in the skin layer(s).

III. Articles

The water-sensitive film of the present invention may be used in a wide variety of applications. For example, as indicated above, the film may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes. When employed in the absorbent article, the film of the present invention may form the backsheet, topsheet, release liner, waist band, side panel, and/or any other material or component of the absorbent article as is well known in the art.

Of course, the water-sensitive film of the present invention is versatile and may also be used with other types of articles of manufacture. For example, the film may be used as a packaging film for a wide variety of products, such as food products, tissues, medical products, garments, absorbent articles (e.g., diapers), and so forth. The film may also be used as a cover to toilets, toilet plungers, etc.

The present invention may be better understood with reference to the following examples.

Test Methods

Tensile Properties:

The strip tensile strength values were determined in substantial accordance with ASTM Standard D638-99. A constant-rate-of-extension type of tensile tester was employed. The tensile testing system was a Sintech 1/D tensile tester, which is available from Sintech Corp. of Cary, N.C. The tensile tester was equipped with TESTWORKS 4.08B software from MTS Corporation to support the testing. An appropriate load cell was selected so that the tested value fell within the range of 10-90% of the full scale load. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of abut 127 millimeters per minute until breakage occurred. The modulus, peak stress, and elongation were measured in the machine direction ("MD") and cross-machine directions ("CD").

Water Disintegration Test:

The rate of film disintegration in tap water was tested using a "slosh box", which has a physical dimension of a 14"×18"×12" high plastic box on a hinged platform. One end of the platform is attached to the reciprocating cam. The typical amplitude is ±2" (4" range), with sloshing occurring at 0.5~1.5 sloshes per second. The preferred action is 0.9~1.3 sloshes per second. During a test, the slosh box rocks up and down with the water inside, "sloshing" back and forth. This action produces a wave front and intermittent motion on a sample susceptible to dispersing in water. To quantify a measurement of sample film disintegration in water, without image analysis, simply timing is sufficient. Three liters of tap water were added into the slosh box and resulted in ~5.5" water depth in the box. A frequency of 3.5 was selected for the testing. Each film sample was cut into 1"×3" size. Three pieces were dropped into the slosh box. The time to disintegrate the sample under the defined conditions was recorded twice for each sample. The average of the time to the sample disintegration is then reported. Generally, films reach an acceptable dispersion point when no piece is larger than 25 $mm^2$ in size within 6 hours of agitation.

Example 1

A range of blends were created containing plasticized polyvinyl alcohol "PVOH" (Aqua-Sol™ 116, which is available from A. Schulman, Inc.) and Firmenich 179132 Fresh Linen fragrance (Firmenich of Geneva, Switzerland). A Thermo Prism Twin Screw Extruder (ThermoElectron Corporation) was used to melt compound the PVOH resin with the fragrance. The PVOH resin pellets were fed into the throat of the extruder using a gravimetric polymer feeder from K-Tron (Pitman, N.J.). The Thermo Prism consists of ten zones at which liquid injection ports exist at zones 4 and 8. As the pellets were added, a liquid injection pump (manufactured by Eldex Laboratories, Inc., Napa, Calif.) was utilized to inject the fragrance oil into the polymer melt at zone 4 of the extruder. Fragrance was added to the water dispersible polymer at 2, 4 and 6% based on the polymer feed rate, and utilized the conditions shown below in Table 1. Strands were cooled as they exited the extruder and subsequently pelletized for film casting.

Film casting was also performed on the Thermo Prism Twin Screw Extruder; however, the strand die was replaced with the film die. Casting conditions are shown below in Table 2.

TABLE 1

Compounding Conditions

| Composition | Extruder Conditions (° C.) Z1 = throat; Z4 = liquid injection; Z10 = strand die | | | | | | | | | | Screw Speed (rpm) | Torque (%) | Polymer Feed Rate (lbs/hr) | Liquid Injection Rate (g/minute) |
| --- | --- | --- | --- | --- | --- | --- | --- | --- | --- | --- | --- | --- | --- | --- |
|  | Zone 1 | 2 | 3 | 4 | 5 | 6 | 7 | 8 | 9 | 10 |  |  |  |  |
| Aquasol PVOH + 2% Fragrance (Firmenich 179132) | 180 | 200 | 200 | 210 | 210 | 210 | 230 | 230 | 180 | 170 | 130 | 60-70 | 3.92 | 0.608 |
| Aquasol PVOH + 4% Fragrance (Firmenich 179132) | 180 | 200 | 200 | 210 | 210 | 210 | 230 | 230 | 180 | 170 | 130 | 65-70 | 3.84 | 1.21 |
| Aquasol PVOH + 6% Fragrance (Firmenich 179132) | 180 | 200 | 200 | 210 | 210 | 210 | 230 | 230 | 180 | 170 | 130 | 50-60 | 3.76 | 1.78 |

TABLE 2

Film Casting Conditions

| Composition | Dried/ Undried | Extruder Conditions (° C.) Z1 = throat; Z11 = cast film die | | | | | | | | | | | Screw Speed (rpm) | Torque (%) | Polymer Feed Rate (lbs/hr) |
| --- | --- | --- | --- | --- | --- | --- | --- | --- | --- | --- | --- | --- | --- | --- | --- |
|  |  | Zone 1 | 2 | 3 | 4 | 5 | 6 | 7 | 8 | 9 | 10 | 11 |  |  |  |
| Aquasol PVOH | Undried | 170 | 180 | 230 | 230 | 210 | 210 | 210 | 200 | 200 | 180 | 185 | 150 | 50 | 5 |
| Aquasol PVOH + 2% Fragrance (Firmenich 179132) | Dried | 170 | 180 | 230 | 230 | 210 | 210 | 210 | 200 | 200 | 190 | 185 | 150 | 50 | 5 |
| Aquasol PVOH + 4% Fragrance (Firmenich 179132) | Dried | 170 | 180 | 230 | 230 | 210 | 210 | 210 | 200 | 200 | 190 | 185 | 150 | 30-50 | 3 |
| Aquasol PVOH + 6% Fragrance (Firmenich 179132) | Dried | 170 | 180 | 230 | 230 | 210 | 210 | 210 | 200 | 200 | 190 | 185 | 150 | 30-50 | 3 |

The Fresh Linen scent was easily detected in the resulting films.

Example 2

Blends were created using Aqua-Sol™ 116 PVOH obtained from A. Schulman of Akron, Ohio and Firmenich 447779 fragrance (menthol, eucalyptus and camphor) obtained from Firmenich of Geneva, Switzerland. The starch-based and PVOH resins were fed into the extruder throat via a gravimetric feeder and melt blended with the fragrances, which were liquid injected into the extruder at zone 4. Instead of extruding fragranced polymer strands, pelletizing, and then film casting, extrusion and film casting were performed in one step utilizing the cast film die attached to the Twin Screw Extruder (zone 11). The extrusion conditions are shown below in Table 3.

TABLE 3

Extrusion Conditions

| Composition | Extruder Conditions (° C.) Z1 = throat; Z4 = liquid Injection; Z11 = strand die | | | | | | | | | | | Screw Speed (rpm) | Torque (%) | Polymer Feed Rate (lbs/hr) | Liquid Injection Rate (g/minute) |
| --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 |  |  |  |  |
| Aquasol PVOH + 4% Fragrance (Firmenich 447779) | n/a | 170 | 180 | 230 | 230 | 210 | 210 | 210 | 200 | 200 | 190 | 185 | 150 | 40-50 | 3.7 |
| Aquasol PVOH + 4% Fragrance (Firmenich 4477779) | n/a | 170 | 180 | 230 | 230 | 210 | 210 | 210 | 200 | 200 | 190 | 185 | 150 | 40-50 | 1.85 |

Firmenich 447779 was detected, but was most prominent when the film was wet and had begun dissolving.

Example 3

A variety of lightly fragranced starch-based films were created. Thermoplastic starch ("TPS") was created by dry blending 70% native corn starch from Cargill with 30% sorbitol from Archer-Daniel-Midland Co., Decatur, Ill. and 2% P40S surfactant (Kao Co., Japan). Thirty-percent Elvanol™ 51-05 polyvinyl alcohol from DuPont was then added to the Corn TPS to create an overall 70/30 Corn TPS/PVOH blend. This 70/30 blend was fed into the extruder throat via a K-Iron powder feeder. Firmenich 179132 Fresh Linen was added to the extruder at zone 4 and incorporated into the thermoplastic melt. The resulting polymer strands were cooled and pelletized before film casting. Table 4 below describes the extrusion conditions during the thermoplastic starch-fragrance addition converting process.

TABLE 4

Extrusion Conditions

| Composition | Extruder Conditions (° C.) Z1 = throat; Z4 = liquid injection; Z10 = strand die | | | | | | | | | | Screw Speed (rpm) | Torque (%) | Powder Feed Rate (lbs/hr) | Liquid Injection Rate (g/minute) |
| --- | --- | --- | --- | --- | --- | --- | --- | --- | --- | --- | --- | --- | --- | --- |
| | Zone 1 | 2 | 3 | 4 | 5 | 6 | 7 | 8 | 9 | 10 | | | | |
| 70/30 Corn TPS/PVA + 0.6% Fragrance (Firmenich 179132) | 90 | 120 | 150 | 160 | 160 | 160 | 140 | 130 | 125 | 120 | 150 | 75 | 3.5 | 0.15 |
| 70/30 Corn TPS/PVA + 2% Fragrance (Firmenich 179132) | 90 | 120 | 150 | 160 | 160 | 150 | 140 | 130 | 125 | 120 | 150 | 50 | 3.5 | 0.51 |

Corn TPS consists of 70% Native Corn Starch from Cargill, 30% Sorbitol and 2% P40S Surfactant (2% of corn starch weight). Corn TPS was dry blended with Elvanol 51-05 PVA and placed in the powder feeder for thermoplastic converting.

The fragranced Corn TPS/PVOH resin was then dry blended with ECOFLEX® F BX 7011 (BASF) before blown film casting. Three blends were created: 1) 56/24/20 Corn TPS/PVOH/ECOFLEX® (majority TPS blend), 2) 49/21/30 Corn TPS/PVOH/ECOFLEX®, and 3) 15/6/79 Corn TPS/PVOH/ECOFLEX® (majority ECOFLEX® blend). The blown film processing conditions are shown below in Table 5, while the film tensile property results are shown in Table 6.

TABLE 5

Blown Film Processing Conditions

| Composition | Extruder Conditions (° C.) | | | | | Melt Temp. (° C.) |
| --- | --- | --- | --- | --- | --- | --- |
| | Zone 1 | 2 | 3 | 4 | 5 | |
| 56/24/20 Corn TPS/PVOH/Ecoflex (0.6% Fresh Linen Firmenich 179132) | 160 | 170 | 175 | 180 | 180 | 184 |
| 49/21/30 Corn TPS/PVOH/Ecoflex (2% Fresh Linen Firmenich 179132) | 160 | 170 | 175 | 180 | 180 | 184 |
| 15/6/79 Corn TPS/PVOH/Ecoflex (2% Fresh Linen Firmenich 179132) | 160 | 170 | 175 | 180 | 180 | 184 |

TABLE 6

Film Tensile Properties

| Composition Sample ID | Mean | Thickness (mil) | | Modulus (MPa) | | Peak Stress (MPa) | | Strain at Break (%) | | Total Energy Absorbed (J/cm 3) | |
| --- | --- | --- | --- | --- | --- | --- | --- | --- | --- | --- | --- |
| | | MD | CD | MD | CD | MD | CD | MD | CD | MD | CD |
| 56/24/20 Corn TPS/PVOH/Ecoflex (0.6% Fresh Linen Firmenich 179132) | | 1.0 | 1.1 | 757 | 788 | 13 | 12 | 13 | 9 | 1.4 | 0.8 |
| 21/79 Corn TPS with PVOH/Ecoflex (2% Fresh Linen Firmenich 179132) | | 1.3 | 1.0 | 527 | 425 | 13 | 12 | 27 | 206 | 28 | 19 |

As indicated, films made with a majority of Ecoflex® had better film properties than those with a majority of Corn TPS. Both films had the characteristic Fresh Linen scent, although the scent was much stronger in the film that contained 2% fragrance. While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A water-sensitive fragranced film formed from a melt-processed blend of:
    (1) a first water-soluble polymer, wherein the first water-soluble polymer includes a chemically modified starch, wherein the chemically modified starch is a hydroxyalkyl starch;
    (2) a second water-soluble polymer, wherein the second water-soluble polymer is a vinyl alcohol polymer;
    (3) a biodegradable polyester, wherein the biodegradable polyester includes an aliphatic-aromatic copolyester;
    (4) at least one liquid fragrance; and
    (5) a plasticizer, wherein the plasticizer consists of a polyhydric alcohol, and wherein the liquid fragrance has a boiling point at atmospheric pressure of from about 125° C. to about 350° C.

2. An absorbent article comprising the film of claim 1, wherein the absorbent article comprises a body portion that includes a liquid permeable topsheet, a generally liquid impermeable backsheet, and an absorbent core positioned between the backsheet and the topsheet.

3. A package comprising the film of claim 1.

4. The film of claim 1, wherein the vinyl alcohol polymer is a vinyl alcohol homopolymer.

5. The film of claim 1, wherein the vinyl alcohol polymer has a degree of hydrolysis of from about 80 mole % to about 95 mole %.

6. The film of claim 1, wherein the fragrance has a boiling point at atmospheric pressure of from about 175° C. to about 250° C.

7. The film of claim 1, wherein fragrances constitute from about 0.1 wt. % to about 15 wt. % of the film.

8. The film of claim 1, wherein fragrances constitute from about 1 wt. % to about 5 wt. % of the film.

9. The film of claim 1, wherein the first water-soluble polymer and the second water-soluble polymer have a solution viscosity of from about 50 to about 800 milliPascal seconds.

10. The film of claim 1, wherein the first water-soluble polymer and the second water-soluble polymer constitute from about 40 wt. % to about 99.9 wt. % of the film.

11. The film of claim 1, wherein the film is formed by supplying the water-soluble polymer and plasticizer to an extruder and directly injecting the liquid fragrance into the extruder to form a blend comprising the water-soluble polymer and the fragrance, wherein injection of the liquid fragrance is accomplished without pre-compounding the fragrance.

12. The film of claim 1, wherein the polyhydric alcohol is a sugar, a sugar alcohol, a polyol, or a combination thereof.

13. The film of claim 1, wherein the first water-soluble polymer constitutes from 15 wt. % to 56 wt. % of the film.

14. The film of claim 1, wherein the second water-soluble polymer constitutes from 6 wt. % to 24 wt. % of the film.

15. The film of claim 1, wherein the biodegradable polyester constitutes from 20 wt. % to 70 wt. % of the film.

* * * * *